United States Patent [19]
Williams et al.

[11] Patent Number: 5,898,081
[45] Date of Patent: Apr. 27, 1999

[54] CHEMICAL PROCESS

[75] Inventors: Alfred Glyn Williams, Binfield; Nicholas Russell Foster, Bracknell, both of United Kingdom

[73] Assignee: Zeneca Limited, United Kingdom

[21] Appl. No.: 08/382,042

[22] PCT Filed: Jul. 28, 1993

[86] PCT No.: PCT/GB93/01593

§ 371 Date: Feb. 9, 1995

§ 102(e) Date: Feb. 9, 1995

[87] PCT Pub. No.: WO94/05622

PCT Pub. Date: Mar. 17, 1994

[30] Foreign Application Priority Data

Aug. 27, 1992 [GB] United Kingdom ............ 9218241

[51] Int. Cl.$^6$ .................................................. C07C 69/76
[52] U.S. Cl. ........................................................... 560/60
[58] Field of Search .................................................. 560/60

[56] References Cited

U.S. PATENT DOCUMENTS

| | | |
|---|---|---|
| 4,723,034 | 2/1988 | Schirmer et al. . |
| 5,008,275 | 4/1991 | Klausener et al. . |
| 5,036,085 | 7/1991 | Heinemann et al. . |
| 5,114,959 | 5/1992 | Klausener et al. . |
| 5,137,898 | 8/1992 | Klausener et al. . |
| 5,182,295 | 1/1993 | Benoit et al. . |
| 5,189,063 | 2/1993 | Klausener et al. . |

FOREIGN PATENT DOCUMENTS

| | | |
|---|---|---|
| 0 178 826 | 4/1986 | European Pat. Off. . |
| 0 243 012 | 10/1987 | European Pat. Off. . |
| 0 273 572 | 7/1988 | European Pat. Off. . |
| 0 329 011 | 8/1989 | European Pat. Off. . |
| 0 473 980 | 3/1992 | European Pat. Off. . |

OTHER PUBLICATIONS

Dehmlow, E. V., "Phase–Transfer Catalyzed Two–Phase Reactions in Preparative Organic Chemistry", Angew. Chem. (Int. Edtn.), vol. 13, No. 3, 170 [1974].

Dockx, Jozef, "Quaternary Ammonium Compounds in Organic Synthesis", Synthesis, 1973, pp. 441–456.

Starks, Charles, M., "Phase–Transfer Catalysis. I. Heterogeneous Reactions Involving Anion Transfer by Quaternary Ammonium and Phosphonium Salts", Journal of Americal Chemical Society, 93:1, Jan. 13, 1971, pp. 195–199.

*Primary Examiner*—Paul J. Killos
*Attorney, Agent, or Firm*—Marian T. Thomson

[57] ABSTRACT

"One-pot" process for preparing methyl 2-(2-methylphenyl)-3-methoxypropenoate by the formylation and subsequent methylation of methyl o-tolylacetate in an aromatic hydrocarbon solvent in the presence of an alkali metal base and a phase transfer catalyst. The product of the process is useful as an intermediate in the manufacture of fungicides such as those described in EP 370629.

10 Claims, No Drawings

CHEMICAL PROCESS

This invention relates to a chemical process and more particularly to an improved process for the preparation of methyl 2-(2-methylphenyl)-3-methoxypropenoate from methyl 2-methylphenylacetate.

A process for preparing methyl 2-(2-methylphenyl)-3-methoxypropenoate by the formylation of methyl 2-methylphenylacetate and methylation of the methyl 2-formyl-(2-methylphenyl)acetate so formed, is described in EP-A-0203606. The formylation is carried out in absolute ether in the presence of sodium hydride. The formylated material is isolated and methylated with dimethylsulphate in acetone in the presence of potassium carbonate.

Similar methods for preparing other compounds containing the 2-linked methyl 3-methoxypropenoate group are widely reported in recent patent literature beginning with EP-A-0178826. Mostly, the formylation and methylation steps are carried out separately, often in N,N-dimethylformamide (DMF) solvent. Methods of carrying out the two steps in a "one-pot" process are, however, also described in, for example, EP-A-0243012, EP-A-0480795, EP-A-0329011 and EP-A-0473980. In these methods DMF is again used as the solvent and sodium hydride or sodium methoxide as the base. In EP-A-0273572 a formylation method is described in which toluene is used as the solvent but the sodium salt of the formylated material is isolated before methylation in DMF.

According to the present invention there is provided an improved process for the preparation of methyl 2-(2-methylphenyl)-3-methoxypropenoate which comprises contacting methyl 2-methylphenylacetate with methyl formate in an aromatic hydrocarbon solvent in the presence of an alkali metal base and a phase transfer catalyst, and thereafter methylating, without isolation, the product so formed in the presence of water.

The aromatic hydrocarbon solvent used in the process of the invention is suitably an alkylbenzene, typically a methylbenzene, solvent, for example xylene or toluene.

The alkali metal base is suitably an alkali metal alkoxide, typically a sodium or potassium $C_{1-4}$ alkoxide, for example sodium methoxide, sodium ethoxide or sodium t-butoxide.

By the term "phase transfer catalyst" is meant a substance which, being at least partly present in or wetted by a first (usually organic) phase promotes reaction between a reactant in the first phase and a reactant which it transfers from a second (usually aqueous but sometimes solid) phase to the first phase. After reaction, the phase transfer catalyst is released for transferring further reactant. Phase transfer catalysts are reviewed by E. V. Dehmlow in Angewante Chemie (International Edition) Vol. 13, No.3, 1974, page 170. Other reviews are by Jozef Dockx in Synthesis 1973 at pages 441–456 and by C. M. Starks in the Journal of the American Chemical Society (93) 1, Jan. 13 1971, pages 195–199.

Suitably the phase transfer catalyst is a quaternary ammonium or phosphonium salt preferably containing bulky organic groups, usually alkyl or aralkyl groups, to make it soluble in the organic phase. The molecular geometry of the quaternary ammonium or phosphonium cation is thought not to be of prime importance, but to confer preferential solubility in the first organic phase rather than the second phase. It is preferred that the phase catalyst is a tetraalkyl or aralkyl(eg benzyl)trialkyl ammonium or phosphonium salt in which the total number of carbon atoms attached to each nitrogen or phosphorus atom is greater than 10. There is little advantage in the number being above 70.

It is especially preferred that the number should be in the range of from 16 to 40.

Examples of quaternary ammonium salts are: cetyltrimethylammonium bromide, dicetyldimethylammonium chloride, octyltributylammonium bromide, trioctylmethylammonium chloride, benzyldimethyllaurylammonium chloride, benzyltributylammonium chloride, dilauryldimethylammonium chloride, tetrabutylammonium sulphate and dieicosyldimethylammonium chloride. Tetrabutylammonium bromide is particularly suitable. Examples of quaternary phosphonium salts are cetyltripropylphosphonium bromide and triphenylethylphosphonium bromide.

Other phase transfer catalysts which may be suitable include crown ethers and polyethylene glycols.

Methylation of the unisolated product of the first part of the invention process, viz. the alkali metal salt of methyl 2-(2-methylphenyl)-3-hydroxypropenoate, may be carried out with any suitable methylating agent of the formula $CH_3L$, where L is a leaving group, such as a halide, for example bromide or iodide, or the methyl sulphate anion. Dimethyl sulphate is convenient to use.

The starting material, methyl 2-methylphenylacetate, is readily obtained by esterification of 2-methylphenylacetic acid, which is commercially available. Conveniently the esterification can be carried out in the same solvent as used in the invention process, so that a solution of the ester, after removal of water-soluble salts and drying, can be used directly.

The process of the invention is conveniently carried out by adding a dried solution of methyl 2-methylphenylacetate in the aromatic hydrocarbon solvent to a stirred suspension of the alkali metal base in more of the same solvent, which contains the phase transfer catalyst, at a temperature of from 0° C. to 15° C. The methyl formate is added and the reaction mixture stirred for several hours at room temperature. Water is then added to the reaction mixture, preferably keeping the temperature below 25° C., followed by the methylating agent in more of the same aromatic hydrocarbon solvent.

After stirring at room temperature the reaction mixture is acidified and the organic phase separated from the aqueous phase and dried and concentrated to yield methyl 2-(2-methylphenyl)-3-methoxypropenoate, usually as a mixture of the (E)- and (Z)-isomers, in which the (E)-isomer predominates.

The solution of methyl 2-methylphenylacetate used in the invention process is conveniently prepared by adding a methylating agent, such as dimethyl sulphate, to a mixture of 2-methylphenylacetic acid, a base, such as sodium hydrogen carbonate, and a phase transfer catalyst in the same aromatic hydrocarbon solvent as is to be used in the invention process. After removing unwanted salts with water, the organic phase containing the methyl 2-methylphenylacetate starting material can be dried by azeotropic distillation.

The product of the process, methyl 2-(2-methylphenyl)-3-methoxypropenoate, is a useful chemical intermediate in the manufacture of fungicides of the type described in, for example, EP-A-0370629. When brominated by, for instances the process described in our co-pending UK application No 9218242.7 the fungicidally preferred (E)-isomer of methyl 2-(2-bromomethylphenyl)-3-methoxypropenoate is formed whether or not the (E)- or (Z)-isomer of the unbrominated precursor, or a mixture of isomers, is used. It is, therefore, no disadvantage of the invention process that a mixture of the (E)- and (Z)-isomers of the unbrominated material is obtained. Typically the mixture will contain the (E)- and (Z)-isomers in the ratio of 85:15 to 90:10.

The process of the invention enables the formylation and methylation steps to be carried out in the same reaction vessel, in a "one-pot" process. It also provides a 'streamlined' process from 2-methylphenylacetic acid, enabling the esterification solution to be used directly in the invention process after removing water-soluble impurities.

The invention is illustrated by the following example in which solutions, when dried, were dried over magnesium sulphate and, when concentrated, were concentrated under reduced pressure. Materials were dried before use, as appropriate. The following abbreviations are used throughout:

GC=gas chromatography

HPLC=high performance liquid chromatography

EXAMPLE

This Example illustrates a 'streamlined' route to (E)-methyl 2-(2--methylphenyl)-3-methoxypropenoate from o-tolylacetic acid (2-methylphenylacetic acid).

Esterification Step

Dimethyl sulphate (6.93 g) was added over 5 minutes to a mixture of o-tolylacetic acid (7.57 g), sodium hydrogen carbonate (6.3 g) and tetra-butylammonium bromide (0.4 g) in toluene (35 ml) held at 35° C. The reaction mixture was then heated to 50° C. and held at that temperature for 8.5 hours. Water (25 ml) was added at 45° C., and the liquid phases were separated. After washing with water and brine, the organic phase was diluted with toluene and the solution dried by azeotroping/distilling out excess solvent.

Formylation Step

The solution from the esterification step (containing ester, 7.68 g in toluene, 15 ml, by GC estimation) was added over 15 minutes, to a stirred suspension of sodium methoxide (4.93 g) in toluene (25 ml) containing tetrabutylammonium bromide (0.5 g), at 4° C. to 10° C. The resulting mixture was stirred for a further 15 minutes at 9° C. to 10° C.

Methyl formate (5.48 g) was added over 15 minutes at 10° C. to 15° C., followed by stirring at 18° C. to 21° C. for 6 hours.

Methylation Step

Water (5 ml) was added to the mixture from the previous step, holding the temperature below 25° C., then dimethyl sulphate (6.05 g) in toluene (10 ml) was added dropwise, again below 25° C. The reaction was stirred thereafter at room temperature for 16.5 hours.

After acidification to pH 1 with dilute hydrochloric acid, the phases were separated and the aqueous phase rewashed with toluene. The combined toluene phase was washed with water, dried and concentrated at high vacuum to yield a pale yellow oil (6.4 g), which, on storing at −20° C. then at ambient temperature, became an oily white solid.

Composition of this product, as determined by GC, HPLC and GC-mass spectrometry was:

(E)-methyl 2-(2-methylphenyl)-3-methoxypropenoate, 84%

(Z)-methyl 2-(2-methylphenyl)-3-methoxypropenoate, 14%

We claim:

1. A process for the preparation of methyl 2-(2-methylphenyl)-3-methoxypropenoate which comprises contacting methyl 2-methylphenylacetate with methyl formate in an aromatic hydrocarbon solvent in the presence of an alkali metal base and a phase transfer catalyst, and thereafter methylating, without isolation, the product so formed in the presence of water.

2. A process according to claim 1 in which the aromatic hydrocarbon solvent is a methylbenzene.

3. A process according to claim 1 in which the aromatic hydrocarbon solvent is xylene or toluene.

4. A process according to claim 1 in which the alkali metal base is a sodium or potassium $C_{1-4}$ alkoxide.

5. A process according to claim 1 in which the alkali metal base is sodium methoxide, sodium ethoxide or sodium t-butoxide.

6. A process according to claim 1 in which the phase transfer catalyst is a tetraalkyl or aralkyltrialkyl ammonium or phosphonium salt in which the total number of carbon atoms attached to each nitrogen or phosphorus atom is greater than 10.

7. A process according to claim 6 in which the total number of carbon atoms attached to the nitrogen or phosphorus atom of the phase transfer catalyst is in the range of from 16 to 40.

8. A process according to claim 1 in which the phase transfer catalyst is tetrabutyl ammonium bromide.

9. A process as claimed in claim 1 comprising the steps of:

(i) adding a dried solution of methyl 2-methylphenylacetate in the aromatic hydrocarbon solvent to a stirred suspension of the alkali metal base in more of the same solvent, which contains the phase transfer catalyst, at a temperature of from 0° C. to 15° C.;

(ii) adding to the mixture formed in step (i) methyl formate; and (iii) adding water to the reaction mixture formed in step (ii), keeping the temperature below 25° C., followed by the methylating agent in more of the same aromatic hydrocarbon solvent.

10. A process according to claim 1 in which the methyl 2-methylphenylacetate is prepared as a solution by adding a methylating agent to a mixture of 2-methylphenylacetic acid, a base, and a phase transfer catalyst in the same aromatic hydrocarbon solvent as is to be used later in the process.

* * * * *